US00PP37163P2

(12) United States Plant Patent
Carter

(10) Patent No.: US PP37,163 P2
(45) Date of Patent: Dec. 16, 2025

(54) ***SALVIA* PLANT NAMED 'Ignition Orange'**

(50) Latin Name: ***Salvia* x *jamensis***
Varietal Denomination: Ignition Orange

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 0 days.

(21) Appl. No.: 19/058,226

(22) Filed: Feb. 20, 2025

(51) Int. Cl.
*A01H 5/02* (2018.01)
*A01H 6/50* (2018.01)

(52) U.S. Cl.
USPC ..... Plt./475
CPC ..... *A01H 6/508* (2018.05); *A01H 5/02* (2013.01)

(58) Field of Classification Search
USPC ..... Plt./475
See application file for complete search history.

(56) References Cited

PUBLICATIONS https://www.instagram.com/national_garden_bureau/p/DDh5QKaBgeS/ (Retrieved from the Internet on May 21, 2025).*

* cited by examiner

*Primary Examiner* — Susan Mccormick Ewoldt
(74) *Attorney, Agent, or Firm* — Weatherly IP Solutions, LLC; James M. Weatherly

(57) ABSTRACT

A new cultivar of *Salvia* x *jamensis* named 'Ignition Orange' that is distinguishable by its compact low-growing well-branched plant habit and flowers which are large for the species and are peach-orange in color and borne over a long blooming season. The leaves of 'Ignition Orange' are small, glossy and dark green in color.

2 Drawing Sheets

Genus and species: *Salvia* x *jamensis.*
Variety denomination: 'Ignition Orange'.

BACKGROUND

The present disclosure relates to a new and distinct cultivar of *Salvia* plant, also known as a sage or James Sage, a perennial that is grown for use as an ornamental landscape and container plant. The new variety is known botanically as *Salvia* x *jamensis* and will be referred to hereinafter by the cultivar name 'Ignition Orange'.

'Ignition Orange' originated and was selected from a population of hybrid seedlings from a *Salvia* breeding program, which was started in 2010. The breeding program was conducted in the inventor's greenhouse nursery in Elk, California. The aim of the breeding program is to develop a uniform series of compact free-flowering varieties of *Salvia* x *jamensis* each with similar plant habits and flowering characteristics but with distinctly different flower colors. *Salvia* x *jamensis* is an inter-species hybrid between the species *Salvia greggii* and the species *Salvia microphylla*. Many varieties of *Salvia greggii* have been released in a wide range of flower colors from white through pink to bright red. Varieties of the species *Salvia microphylla* are noted for their small dark green, glossy elliptical leaves. 'Ignition Orange' was selected from seedlings which resulted from the controlled hybridization using pollen collected from the stigma of a previously raised, unnamed and unreleased, known to the Inventor as 'Elk Lemon Lite'. The collected pollen was applied to an unnamed and unreleased seedling as female parent. seedling. Seed from the female parent was grown out, and one seedling, the instant variety, was selected for its unusual peach-orange colored flowers which are borne on compact low-growing plants with dark green small glossy leaves.

'Ignition Orange' was first asexually propagated in 2020 in a greenhouse at the inventor's nursery in Elk, California using softwood tip cuttings. The inventor has confirmed that 'Ignition Orange' is stable and reproduces true to type in successive generations of asexual reproduction.

SUMMARY

The following traits have been repeatedly observed and represent the distinguishing characteristics of 'Ignition Orange'. 'Ignition Orange' has not been tested under all possible conditions and phenotypic differences may be observed with variations in environmental, climatic, and cultural conditions, without however, any variance in genotype.

1. 'Ignition Orange' exhibits a compact low-growing well-branched plant habit.
2. The flowers of 'Ignition Orange' are large for the species and are peach-orange in color and borne over a long blooming season.

DESCRIPTION OF THE PHOTOGRAPHS

The accompanying color photographs illustrate the overall appearance of the new *Salvia* cultivar 'Ignition Orange' showing the colors as true as it is reasonably possible to obtain in colored reproductions of this type. Photographs were taken in March 2022 in Santa Barbara, California from a one-year-old plant grown outdoors in-ground with sparing drip irrigation. After establishment, the plant received one pinch to stimulate branching. No chemical growth regulators have been applied to the illustrated and observed plant. The colors in the photographs may differ from the color values cited in the detailed botanical description, which more accurately describes the actual colors of the new variety 'Ignition Orange'.

DESCRIPTION OF THE NEW VARIETY

Figure 1:
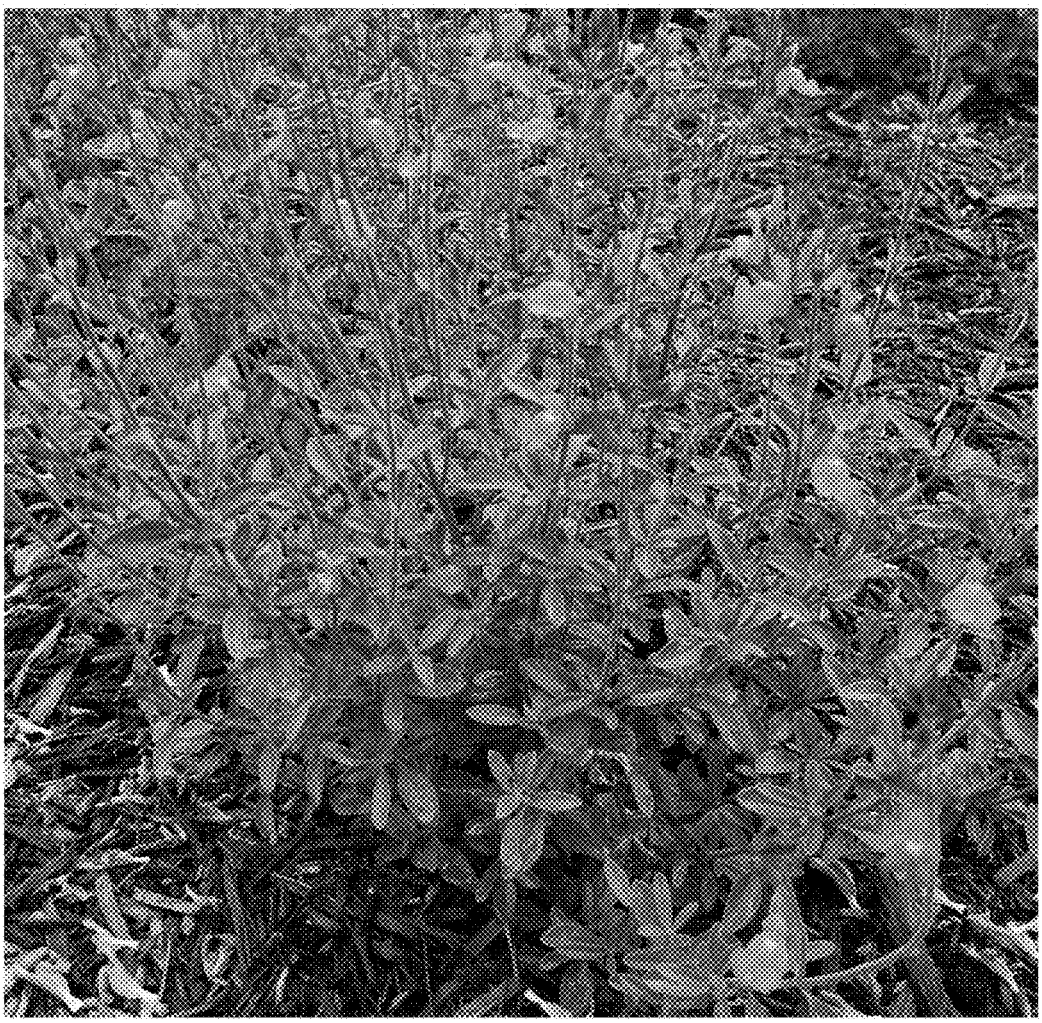
FIG. 1 depicts an entire plant in flower of 'Ignition Orange'.
Figure 2:
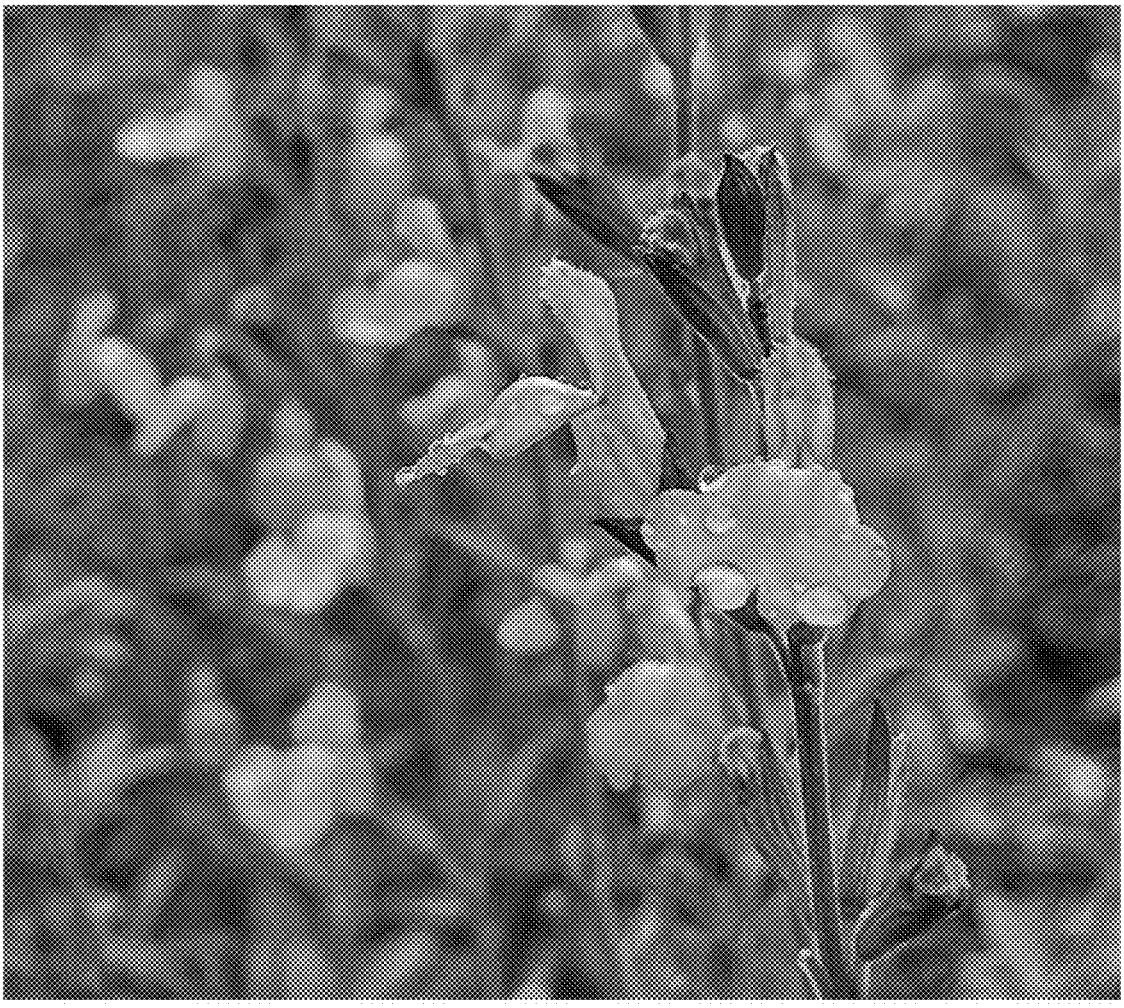
FIG. 2 depicts a close-up view of the inflorescences of 'Ignition Orange' showing the flowers and the terminal bud cluster.

The following detailed descriptions set forth the distinctive characteristics of 'Ignition Orange'. Observations, measurements, values, and comparisons were collected in March 2022 in Santa Barbara, California from a one year old plant which had been growing outdoors in-ground and positioned in full sun in Santa Barbara, California. The observed plant had received one pinch after initial cutting establishment. No chemical growth regulators had been applied. Color determinations were made in accordance with The 2007 Royal Horticultural Society Colour Chart from London England, except where general color terms of ordinary dictionary significance are used.

Classification:

*Family*.—Lamiaceae.

*Genus*.—*Salvia*.

*Species*.—X *jamensis*.

*Common name*.—Sage or James Sage.

Parentage:

*Female parent*.—An unnamed and unreleased plant of *Salvia* x *jamensis* retained in the inventor's collection of previously raised seedlings.

*Male parent*.—*Salvia* x *jamensis* 'Elk Lemon Lite' previously raised by the inventor and unpatented.

Plant:

*Propagation method*.—Softwood tip cuttings.

*Rooting system*.—Fine and fibrous.

*Vigor*.—Moderate vigor.

*Time to develop roots*.—5 days are needed for a cutting to develop roots at recommended rooting temperature of 20° to 22° Centigrade.

*Crop time*.—Approximately 12 weeks are required to produce a budded and flowering plant for in-ground landscape planting or for production in ornamental containers from one quart size and upwards. Larger containers require a longer period of growth in order to fill out. Flowering will continue throughout spring, summer and fall.

*Suggested container size*.—Quart to one-gallon container.

*Use*.—Ornamental for use as a landscape plant or container plant.

*Type*.—Perennial.

*Overall dimensions*.—After one year's growth in a 3.7 gallon container, 60 cm in height, including the inflorescence, and 60 cm in diameter.

*Cultural requirements*.—Grow in full sun with moderate water and well-draining soil.

*Hardiness*.—USDA Zone 7.

*Form*.—Low-growing bush.

*Growth habit*.—Compact.

*Blooming season*.—From one month after breaking spring dormancy to first frost.

*Lastingness of blooms*.—Inflorescence has some flower for 14 days, individual flowers last for 2 to 3 days.

Stems (below first pinch):

*Condition*.—Lignified.

*Bark*.—Papery, splitting.

*Shape*.—Round.

*Length*.—1 cm to 2 cm.

*Diameter*.—4 mm.

*Bark color*.—N199A.

*Stem color* (*where exposed beneath split bark*).—143C.

*Shape*.—Square, edges rounded.

*Texture*.—Coriaceous.

Branches:

*Quantity*.—Approximately 40, of which 6 to 8 are primary branches and 30 or more are secondary branches.

*Shape*.—Square, corners rounded.

*Length*.—12 cm to 15 cm measured to base of inflorescence.

*Width*.—3 mm at base then reducing to 2 mm at base of inflorescence.

*Internode length*.—Varies between 25 mm (primary branches), and 12 mm (secondary branches).

*Color*.—143C with dull brown-red anthocyanin coloration on one or two faces of the lower internodes. Anthocyanin color, 166B.

Leaves:

*Type, arrangement*.—Simple, opposite.

*Attachment*.—Sessile on emergence becoming slightly petiolate when leaves fully expanded.

*Quantity per branch*.—6 to 8 pairs.

*Shape*.—Elliptic, inwardly folded along midrib, sulcate overall.

*Length*.—Ranges between 20 mm and 27 mm.

*Width*.—Ranges between 5 mm and 8 mm.

*Margin*.—Smooth, entire.

*Thickness*.—Moderately thick, slightly stiff.

*Venation*.—Pinnate, midrib slightly sulcate.

*Texture* (*both surfaces*).—Smooth, glabrous, matte.

*Color*.—Adaxial surface: 137A. Abaxial surface: N138C.

*Apex*.—Acute.

*Base*.—Cuneate.

*Fragrance*.—Pleasant sage fragrance when rubbed.

*Stipules*.—Present in one or two pairs at each leaf axil. Small, sessile, elliptic, 2 mm-3 mm in length and 1.5 mm to 2 mm in width. Margins smooth, entire, color 137A (adaxial surface), N138C (abaxial surface), surfaces smooth, glabrous.

Petiole (where present, on fully developed leaves):

*Shape*.—Terete.

*Length*.—4 mm.

*Diameter*.—1.5 mm.

*Texture*.—Very lightly puberulent.

*Color*.—138C.

Peduncle:

*Length*.—18 mm.

*Shape*.—Square.

*Width*.—2 mm.

*Texture*.—Puberulent.

*Color*.—147B.

Inflorescence:

*Type*.—Terminal raceme. Flowers arranged in pairs, opposite, outward facing, rotated 30-40 degrees apart.

*Length.*—8 cm to 10 cm.
*Width.*—5 cm.

Pedicel:
*Length.*—6 mm.
*Diameter.*—1.0 mm to 1.5 mm.
*Texture.*—Puberulent.
*Color.*—N187B.

Calyx:
*Shape.*—Campanulate, flared toward the apex.
*Length.*—15 mm.
*Diameter at base.*—2 mm.
*Width.*—8 mm between sepal apices.

Sepals:
*Quantity.*—2, one upper, one lower, substantially longitudinally fused.
*Length.*—15 mm.
*Width.*—5 mm when flattened.
*Shape.*—Sulcate.
*Apex.*—Acuminate.
*Base.*—Truncate.
*Margin.*—Entire.
*Texture.*—Adaxial surface: Puberulent, longitudinally ribbed. Ribs 1 mm apart, raised less than 0.1 mm. Abaxial surface: Glabrous, longitudinal depressions.
*Color.*—Adaxial surface: 152D except N199B where ribbed. Abaxial surface: 153A. Rib color N199B. Sepal color between ribs: 152D.

Flowers:
*Quantity.*—8 to 10 opposite pairs.
*Shape.*—Tubular, two-lipped.
*Dimensions.*—Length (from base of corolla tube to apex of upper lip): Up to 25 mm. Width (maximum width of lower lip): Up to 32 mm.
*Fragrance.*—Pleasant sage fragrance.

Bud:
*Shape.*—Hemispherical on emergence from calyx, becoming cylindrical with rounded apex immediately prior to opening.
*Bud height on emergence.*—4 mm.
*Bud diameter at calyx on emergence.*—3 mm.
*Surface.*—Strongly pubescent, especially apex. Hairs dense, fine, 1 mm in length, color 31B.
*Bud color.*—31A.

Corolla and tube (only visible when pulled out from calyx):
*Shape.*—Tubular.
*Length.*—17 mm including corolla tube length 3 mm.
*Width.*—3 mm.
*Texture.*—Glossy, glandular.
*Color* (*both surfaces*).—71A, except NN155D and translucent at tube base becoming N155D as base adjoins colored petals.

Petals:
*Quantity.*—2.
*Arrangement.*—One upper petal borne almost vertically, diverging from one lower mostly horizontal petal which appears as a large prominent lip with two lateral lobes fused to the lip and to each other. Hooded upper petal diverges from lower petal lobe around or slightly above midpoint of flower.
*Upper petal.*—Shape: Hooded, abaxial surface concave. Adaxial surface presents rounded protrusion. Aspect: Mostly vertical. Length (from divergence of lower lip to apex of upper lip): 10 mm-12 mm. Width (across hood): 5 mm. Texture: Adaxial surface: Strongly pubescent. Hairs dense at apex, fine, 1 mm in length, color 31A. Upper lip apex: Rounded, with cluster of fine hairs approximately 1 mm in length, hair color 71A. Upper lip base: Truncate. Upper lip margin: Smooth, entire. Upper lip color (adaxial surface): Ranges between 29C and 32C with pale elliptic streaks ranging between near white NN155D and 159D. Adaxial surface: 71A. Abaxial surface: 159D.
*Lower petal* (*lip and lobe pair*).—Shape: Broad cordate with deep apical notch. Aspect: Mostly horizontal with respect to flower. Length: 10 mm from divergence from upper petal to base of apical notch. Width (at widest across lobes: 18 mm to 20 mm. Texture: Adaxial surface: Puberulent. Abaxial surface: Smooth, glabrous, semi-glossy. Apex: Emarginate, depth of notch 2 mm. Base: Truncate. Margin: Entire, gently undulating. Color (lip and lateral lobes, both surfaces): Midway between 31D and 28C. Texture: Adaxial surface: Puberulent. Abaxial surface: Smooth, glabrous, semi-glossy.

Reproductive organs:
*Stamens.*—Quantity: 2.
*Filaments.*—Dimensions: Length: 13 mm, each filament basally fused for 8 mm and free for 5 mm. Diameter: 1 mm. Color: White NN155D suffused very light, translucent orange-white 159D.
*Anthers.*—Shape: Ellipsoid. Length: 1.5 to 2 mm. Width: 0.5 mm. Color: 165B.
*Pollen.*—Amount: Moderate. Color: 163C.
*Pistil.*—Quantity: 1. Stigma: Shape: Asymmetrically forked. Length: Longer fork 5 mm, strongly recurved; shorter fork 2 mm, gently recurved. Diameter 0.75 mm. Color: White NN155D suffused very light, translucent orange-white 159D. Style: Length (excluding stigma): 9 mm. Color: N155A towards base, becoming darker 158D.
*Ovary* (*only observed unfertilized*).—Length: 3 mm. Width: 1.5 mm. Color: 150B.

Seed:
*Quantity.*—Sparse.
*Shape.*—Ovoid.
*Dimensions.*—Length 2 mm, diameter 1 mm.
*Color.*—Speckled, ranging between 165B and N199B.
*Surface.*—Smooth and matte.

Disease and pest susceptibility: Susceptible to aphids (*Aphis gossypii*) when stressed. Generally outgrows most bacterial and viral infections. Resistant to deer and rabbit grazing.

Drought tolerance: Drought tolerant.

COMPARISON WITH PARENTAL LINES AND KNOWN VARIETY

In comparison with the male pollen donor variety, 'Elk Lemon Lite', 'Ignition Orange' exhibits larger flowers with a distinctive peach-orange color. The flowers of 'Elk Lemon Lite' are luminescent pale yellow in color. Both varieties 'Ignition Orange' and 'Elk Lemon Lite' bear glossy dark green small elliptical leaves.

In comparison with the female parent, 'Ignition Orange' bears flowers which are a unique clear peach-orange color. The plant habit of 'Ignition Orange' was selected for its dense and well-branched rounded plant habit whereas the plant habit of the female parent is upright and more open as is typical of the species *Salvia* x *microphylla*. Both varieties 'Ignition Orange' and the unnamed female parent seedling bear glossy dark green small elliptical leaves.

In comparison with the unnamed and unreleased female parent seedling, 'Ignition Orange' bears large flowers which are a unique clear peach-orange color. The flowers of the unnamed and unreleased female parent seedling are smaller, paler yellow and shorter longer lasting than the flowers of 'Ignition Orange'. The plant height of 'Ignition Orange' is shorter than the plant height of the female parent. Both varieties, 'Ignition Orange' and the unnamed female parent seedling bear glossy dark green small elliptical leaves.

'Ignition Orange' is closest in plant habit to, first, *Salvia greggii* 'Cherry Chief' (unpatented) and second to the inventor's variety *Salvia Salvia* x *jamensis* 'Elk Twilight Rosy Glow' (unpatented). Neither of these comparison varieties bears flowers with an orange hue. The flowers of *Salvia* 'Cherry Chief' are multi-colored, chiefly pink. The flowers of *Salvia* x *jamensis* 'Elk Twilight Rosy Glow' are salmon-pink in color. In addition, the mature height of *Salvia Salvia jamensis* 'Elk Twilight Rosy Glow' is 75 cm-1 m, whereas the mature height of 'Ignition Orange' is 60 cm.

I claim:

1. A new and distinct cultivar of *Salvia* Plant Named 'Ignition Orange' as described and illustrated herein.

* * * * *